United States Patent [19]
Beard et al.

[11] Patent Number: 6,022,695
[45] Date of Patent: *Feb. 8, 2000

[54] ANTENATAL RISK ASSESSMENT SCREENING FOR PREGNANCY ABNORMALITIES

[75] Inventors: Andrew Jonathan Beard, High Wycombe; Adrian Charles Dawkes, Windsor; Christopher John Davies, Mid Glamorgan, all of United Kingdom

[73] Assignee: Johnson & Johnson Clinical Diagnostics, Inc., Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/511,942

[22] Filed: Aug. 7, 1995

[30] Foreign Application Priority Data

Aug. 13, 1994 [GB] United Kingdom .................. 9416415

[51] Int. Cl.[7] .................................................. G01N 33/68
[52] U.S. Cl. ........................ 435/7.21; 435/7.94; 436/65; 436/86; 436/87; 436/510; 436/518; 436/811; 436/817; 705/2
[58] Field of Search ................................ 435/7.21, 7.94, 435/436; 436/65, 86, 87, 510, 518, 811, 817; 364/413.09; 705/2

[56] References Cited

U.S. PATENT DOCUMENTS

| | | |
|---|---|---|
| 4,874,693 | 10/1989 | Bogart . |
| 5,716,853 | 2/1998 | Cuckle et al. .......................... 436/510 |

FOREIGN PATENT DOCUMENTS

| | | |
|---|---|---|
| WO 89/00696 | 1/1989 | WIPO . |
| WO 90/0832 | 1/1990 | WIPO . |
| WO 90/08325 | 7/1990 | WIPO . |
| WO 94 12884 | 6/1994 | WIPO . |
| WO-A-95 32431 | 11/1995 | WIPO . |

OTHER PUBLICATIONS

Prenatal Diagnosis, vol. 12, 1992, Chichester, pp. 801–806, Van Lith et al; "Second trimester maternal serum immunoreactive inhibin as a marker for fetal Down's syndrome".
Journal of Endocrinology, vol. 129, No. 2, May, 1991, Bristol, pp. R9–R12, Knight et al.; "Development of a two–site immunoradiometric assay for dimeric inhibin . . . ".
Obstetrics & Gynecology, vol. 83, No. 5, May 1994, New York, NY, pp. 661–664, Van Lith et al.; "First trimester maternal serum immunoractive inhibin . . . ".
Prenatal Diagnosis, vol. 15, No. 4, Apr. 1995, Chichester, pp. 359–362, Wallace et al.; "Evaluation of maternal serum dimetric inhibin . . . ".
American Journal of Human Genetics, vol. 55, No. 3, (Supplment), Sep. 1994, Chicago, p. A9, Canick et al.; "Maternal serum dimeric inhibin is elevated in Down syndrome", Abstract 37.
E. M. Wallace et al, Clin. Endocrinol., 41, 483–486, 1994.
Cuckle et al, Brit. Jour. Obst. Gyn. 94, 387–402 (1987).
Groome et al, Jour. Immunol. Meth. 165, 167–176 (1993).

(List continued on next page.)

*Primary Examiner*—David Saunders

[57] ABSTRACT

Dimeric inhibin concentration can be used in the determination of the risk of a women carrying an unborn child affected by chromosomal abnormalities, e.g. Downs Syndrome. A method for antenatal screening for chromosomal abnormalities is carried out by measuring body fluid taken from a pregnant woman for the level of at least one marker or precursor or metabolite of the marker together with the gestational age of the woman are compared with reference values taken from women carrying fetuses with chromosomal abnormalities and/or women carrying normal fetuses, using dimeric inhibin as a marker. A second marker is the free beta subunit of human chorion gonadotropin. An apparatus for carrying out the method described comprises a computer with a means for comparing the values described.

5 Claims, 6 Drawing Sheets

OTHER PUBLICATIONS

Schneyer et al., "Immunoractive Inhibin . . . Radioimmunoassay", J. Clin. Endocrinol. Metab., 70, 1208–12, 1990.

Lambert–Messerlian et al, "Human Follicular Fluid . . . Proteins", J. Clin. Endocrinology and Metabolism, 78, 443–9, 1994.

Burger, "Inhibin", Reproductive Medicine Reviews, 1, 1–20, 1992.

McLachlan et al, "Circulating Immunoreactive . . . Cycle", J. Clin. Endocrinology and Metabolism, 65, 954–61 1987.

McLachlan et al, "Circulating immunoactive . . . indiction", Fertil. Steril., 48, 1001–08, 1987.

Tovanabutra et al, "The relationship between . . . pregnancy", Clin.Endocrinology, 38, 101–7, 1993.

Spencer et al, "Elevated Levels . . . Syndrome", Anal. Clin, Biochem., 30, 219–20, 1993.

Cuckle et al, "Maternal Serum . . . Pregnancies", Prenatal Diagnosis, 14, 387–90, 1994.

ANTENATAL RISK ASSESSMENT SCREENING FOR PREGNANCY ABNORMALITIES

This invention relates to a method for prenatal or antenatal screening for pregnancy abnormalities such as fetal (particularly chromosomal) abnormalities and to an apparatus for performing the method.

The risk of Downs Syndrome and some other chromosomal abnormalities in a fetus is known to increase with the age of the mother and it is this knowledge which forms the basis for selection of pregnant women for further investigation. Further investigation in the case of Downs Syndrome involves sampling of the amniotic fluid by amniocentesis, a procedure which itself carries a risk for the mother of the fetus, induction of a miscarriage being a recognised hazard of this procedure.

During pregnancy, maternal markers for Downs syndrome are widely used for screening, the most common being alpha-fetoprotein (AFP), human chorionic gonadotrophin (hCG) (either the intact molecule or free beta-subunit of hCG) and unconjugated oestriol (UE3). Disclosures relating to the use of such markers which may be used in combination with maternal age, include U.S. Pat. No. 4,874,693; WO 89/00696 and WO 90/08325.

Maternal screening is based on selecting a subgroup of women who are at the highest risk of giving birth to a child with an abnormality. In these women, the risk of invasive diagnostic procedures are considered to be outweighed by the risk of the abnormality. The risk is calculated by multiplying the a priori age related risk by the likelihood ratio The likelihood ratio is calculated from the relative heights of the multivariate Gaussian distribution functions of the marker analytes in Downs affected and unaffected normal pregnancies, corresponding to the value of the individual marker concentrations by dividing the height of the multivariate Gaussian distribution function for unaffected pregnancies by the height of the multivariate Gaussian distribution function for affected pregnancies.

As the concentrations of the analytes currently in use can vary normally with gestational age the analyte concentrations must be weighted accordingly. In turn with these analytes there is a relatively high dependence on accuracy of the estimation of age of gestation for the effective discrimination of Downs affected pregnancies. Weighting is performed by dividing the concentration of the analyte by the median concentration expected for that particular gestational age in women with unaffected pregnancies. This is termed the multiple of the median (MoM).

A combination of multiple analytes provides more information than any single analyte alone. The likelihood ratios determined from a multivariate combination is the most effective method of deriving information relating to the risk of a woman carrying a Downs affected child.

Inhibin is a dimeric molecule having alpha and beta-subunits covalently linked together via cysteine bridges. The alpha subunit is unique to the inhibin molecule and the beta-subunit has some homology with certain growth factors. In addition to dimeric inhibin, 'free' alpha-subunit forms (termed 'pro-alpha-N alpha C', 'pro-alpha-C' and 'alpha-C') and a beta-beta dimer (termed activin) are known to exist. To date only dimeric inhibin has been shown to confer biological activity and a biological activity for the alpha-subunit has yet to be elucidated. Moreover abundant amounts of immunoreactive alpha-subunit have been identified in biological fluids (Schneyer, Mason, Burton, Ziegner and Crowley, J. Clin. Endocrinol. Metab., 70, 1208–12, 990 and Lambert-Messerlian, Isaacson, Crowley, Sluss and Schneyer, J. Clin. Endocrinology and Metabolism, 78, 433–9, 1994) which are also known to contain immunoreactive dimeric inhibin (Knight, Groome and Beard, J. Endocrinology, 129, R9–R12, 1991).

The role of inhibin is unclear although there is a growing body of evidence that it may act as a regulator of pituitary gonadotrophin secretion or in a local paracrine/autocrine function with specific tissues (review Burger, Reproductive Medicine Reviews, 1, 1–20, 1992). It has been reported that immunoreactive 'alpha-inhibin' is secreted during the menstrual cycle (McLachlan, Robertson, Healy, Burger and de Kretser, J. Clin. Endocrinology and Metabolism, 65, 954–61, 1987), in response to exogenous gonadotrophin stimulation during artificially controlled cycles in women (McLachlon, Robertson, Healy, Burger and de Krestser 1987 and Robertson, Fertil. Steril. 48, 1001–08, 1987) and by the fetal placenta during pregnancy (Tovanabutra, Illingworth, Ledger, Glasier and Baird, Clin. Endocrinology, 38, 101–7, 1993). The term 'immunoreactive alpha-inhibin' is used in this context because all the inhibin assays employed in these studies and the Downs studies described below were either alpha-subunit specific by definition or preferentially cross-react with the free forms of inhibin alpha-subunit (Lambert-Messerlian, Isaacson, Crowley, Sluss and Schneyer, 1994). It is therefore unlikely that immunoreactive alpha-inhibin levels reflect immunoreactive dimeric inhibin levels.

Other studies have investigated 'alpha-inhibin' as a potential marker in maternal serum for the presence of Downs syndrome in the unborn child (van Lith, Pratt, Beekhuis and Mantingh, Prenatal Diagnosis, 12, 801–6, 1992; Spencer, Wood and Anthonyyr Anal. Clin. Biochem., 30, 219–20, 1993, Cuckle, Holding and Jones, Prenatal Diagnosis, 14, 387–90, 1993). At the 5% false-positive detection rate, only 40% of the affected pregnancies were detected by combining alpha-inhibin concentrations with maternal age (van Lith, Pratt, Beekhuis and Mantingh, 1992) and alpha-inhibin concentrations were also highly correlated with free beta-hCG levels (Spencer, Wood and Anthony, 1993) and intact hCG (Cuckle, Holding and Jones, 1993). As a result it was concluded that these findings were likely to argue against the use of alpha-inhibin immunoreactivity as an additional biochemical marker in Downs syndrome screening programmes (Spencer, Wood and Anthony, 1993). Whilst Cuckle et al, 1994 refer to such use as "of limited value".

According to the present invention we provide a method for antenatal screening for pregnancy abnormalities such as fetal (particularly chromosomal) abnormalities in which a sample of maternal body fluid from a pregnant woman is measured for the level of at least one marker and/or a precursor or metabolite of said marker and the measured level of this marker together with the gestational age of the woman are compared with reference values at various gestational ages of the level for the marker in (a) pregnant women carrying fetuses having abnormality(s) subject to the screen and/or b) pregnant women carrying normal fetuses, the comparison being indicative of the risk of the pregnant woman carrying a fetus with an abnormality subject to the screen characterized in that the marker is dimeric inhibin.

Further according to the invention we provide an apparatus comprising means adapted for receiving measurement of a pregnant woman's maternal body fluid level of at least one marker and/or a precursor or metabolite of said marker and computer means for comparing the measurements of this level to sets of reference data to determine pregnancy abnormalities such as fetal (particularly chromosomal) abnormalities characterised in that the marker is dimeric inhibin.

In particular the invention relates to the use of an assay that is capable of discriminating between dimeric inhibin from other inhibin-related proteins such as inhibin alpha-subunit in maternal serum. Such an assay employs antibodies which bind to two unique binding sites expressed on the dimeric inhibin molecule. One antibody binds specifically to an epitope on the beta-subunit and the other antibody binds to the alpha-subunit. When one antibody is used to capture the inhibin molecule and the other antibody is labelled with an appropriate signal generator, a signal will result only when intact dimeric inhibin is present in the sample.

The method and apparatus of the invention are very suitable when dimeric inhibin is measured in combination with measurement of other markers such as intact hCG, alpha-fetoprotein (AFP), unconjugated oestriol (UE3), pregnancy associated plasma protein-A (PAPP-A) or other inhibin related proteins such as activin to determine an index of the risk of an individual woman carrying an affected child. In a preferred form of the invention the measurement of dimeric inhibin is combined with measurement of the free beta subunit of hCG.

The maternal body fluids on which measurements are made include for example, saliva, urine, amniotic fluid a nd particularly blood.

The method and apparatus of the invention can be used for antenatal screening for a wide range of pregnancy abnormalities. These include abnormalities such as ectopic pregnancy and particularly fetal chromosomal abnormalities. The most significant and frequently occurring chromosomal abnormality is Downs Syndrome (Trisomy 21). Other such abnormalities which may be screened for using the invention include Edwards Syndrome (Trisomy 18), Pateaus Syndrome (Trisomy 13), Turner Syndrome, Monosomy X and Kleinefelter's Syndrome. The invention may be used to screen for individual abnormalities or to screen for groups of abnormalities together, for example it could be used to screen for both Downs Syndrome and Edwards Syndrome.

Measurements are carried out and analysed using the method of the invention on blood samples taken during an appropriate period of pregnancy. Preferably the measurements are made on blood samples taken in the first and second trimesters and especially in the period between the beginning of the eighth week and the end of the second trimester. The woman's measured serum value for the individual serum marker is divided by the expected median value found in women with unaffected pregnancies at the same gestational age, to derive the multiple of the median (MOM). The probability that the (MoM) values for the combination of serum markers tested belongs to the multivariate distribution of values found in unaffected pregnancies is calculated. The same calculation is performed by reference to the probability that the individual combination of values forms part of the multivariate distribution found in abnormal pregnancies. The ratio of the two probabilities is termed the likelihood ratio (LR) which indicates the likelihood that an individual woman has an affected pregnancy or not. The degree of separation between the multivariate distributions for affected and unaffected pregnancies changes with gestational age, i.e. there is a continuous change in he manner of calculating probability depending upon the gestational age. This continuous change can be built into the algorithm used in the calculation.

An individual women has an a priori age related risk which is independent of the maternal serum marker concentrations. The woman's age related risk, by Baye's theorem, is modified by multiplying by the likelihood ratio (LR) obtained previously to derive a combined risk. This combined risk may then be used to counsel the woman regarding the relative risk of the abnormality as opposed to the risk of miscarriage associated with a subsequent diagnostic invasive procedure.

The invention is illustrated by the accompanying drawings, relating to the Example which follows them, wherein.

Example

Figure 1:
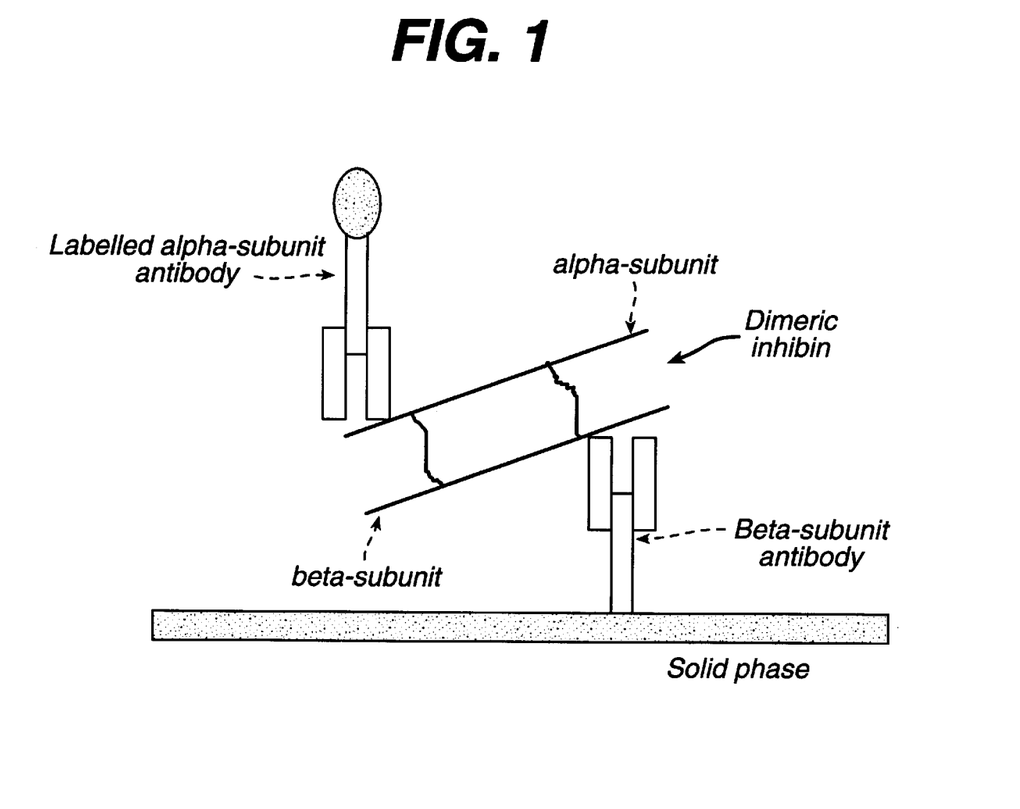
FIG. 1 is a diagrammatic illustration of a specific two-site dimeric inhibin assay.

This invention relates to the use of an assay that is capable of discriminating between dimeric inhibin from other inhibin-related proteins such as inhibin alpha-subunit in maternal serum. The reagents were purchased from Serotec Ltd. 22 Bankside, Station Road, Kidlington, Oxford, OX5 1JE, UK The assay employs antibodies which bind to two unique binding sites expressed on the dimeric inhibin molecule. One antibody binds specifically to an epitope on the beta-subunit and the other antibody binds to the alpha-subunit. When one antibody is used to capture the inhibin molecule and the other antibody is labelled with an appropriate signal generator, a signal will result only when intact dimeric inhibin is present in the sample (FIG. 1).

Samples collected from 21 individual women previously identified as carrying a Downs Syndrome child and an appropriate number of matched controls (individual women carrying an unaffected baby) were assayed in a two-site immunometric assay which is specific for dimeric inhibin (described above). In total 189 control samples were assayed.

The assay was conducted according to the seller's instructions.

Briefly, immediately prior to assay in the dimeric inhibin assay a small volume of sample was oxidized to enhance the assay sensitivity. In this study, the dimeric inhibin assay was designed to capture the inhibin through the beta-subunit and in a second step after a wash, the second antibody (in this assay design it was an enzyme-labelled antibody fragment (Fab)) was contacted with the alpha subunit of the dimeric inhibin. After a further wash to remove the labelled antibody, a signal was produced using the relevant signal mechanism reagents and detected on a conventional ELISA plate reader. The assay was calibrated using gravimetrically prepared dimeric inhibin standards. The levels of dimeric inhibin were determined in test samples containing unknown amounts of dimeric inhibin by comparison with these standards.

To demonstrate the increase in detection rate when inhibin measurements are combined with data from another marker, a second analyte in the maternal serum sample, free beta-hCG, was measured in the same samples using a two-step immunometric assay. Briefly the analyte was contacted by a solid phase monoclonal antibody specific for beta-hCG. After a wash, the captured free-beta-hCG was contacted with an enzyme-labelled polyclonal anti-hCG immunoglobulin preparation. After another wash a signal substrate was added and the signal emitted was detected. Levels of free-beta hCG were estimated in test samples by comparison with calibrators containing known amounts of free-beta hCG.

Results

Table 1 shows assay data for both cases and controls.

TABLE 1

| | SAMPLE ID | Dimeric INHIBIN pg/6 ul | Dimeric inhibin ng/ml | Beta-hCG mIU/ml | | SAMPLE ID | Dimeric INHIBIN pg/6 ul | Dimeric inhibin ng/ml | Beta-hCG mIU/ml | | SAMPLE ID | Dimeric INHIBIN pg/6 ul | Dimeric inhibin ng/ml | Beta-hCG mIU/ml |
|---|---|---|---|---|---|---|---|---|---|---|---|---|---|---|
| PI 1 | 1094 | 39.15 | 6.53 | 56.38 PI 3 | C10 | 3239 | 138.87 | 23.15 | 23.04 PI 5 | C16 | 2595 | 142.64 | 23.11 | 14.20 |
| | 170 | 16694 | 27.82 | 12.73 PI 3 | C10 | 3234 | 116.84 | 19.47 | 5.19 PI 5 | C16 | 2592 | 76.82 | 12.8 | 5.44 |
| C1 | 338 | 524.06 | 87.34 | 31.88 | C10 | 3247 | 11.98 | 30.83 | 10.94 | C16 | 2599 | 153.51 | 25.59 | 11.01 |
| C1 | 567 | 44468 | 74.11 | 3.82 | D10 | 4558 | 60.49 | 111.5 | 63.31 | C16 | 2615 | 123.24 | 20.54 | 6.48 |
| C1 | 668 | 32.74 | 5.46 | 47.04 | C10 | 3260 | 221.72 | 36.95 | 9.13 | C16 | 2600 | 69.14 | 11.36 | 5.94 |
| C1 | 809 | 97.75 | 16.29 | 5.01 | C10 | 3250 | 242.31 | 40.39 | 11.39 | C16 | 2612 | 141.38 | 23.56 | 9.54 |
| C1 | 466 | 371.60 | 61.93 | 8.89 | C10 | 3273 | 167.60 | 27.93 | 7.20 | C16 | 2598 | 157.13 | 26.19 | 12.86 |
| C1 | 1091 | 449.17 | 74.86 | 16.10 | C10 | 3235 | 1.71 | 10.28 | 8.86 | C16 | 2613 | 109.19 | 28.2 | 24.51 |
| D2 | 471 | 406.71 | 61.79 | 5.25 | C10 | 3236 | 326.94 | 54.49 | 33.42 | C16 | 2617 | 129.35 | 21.56 | 7.28 |
| C2 | 472 | 32.03 | 5.34 | 11.35 | C10 | 3248 | 428.95 | 71.16 | 8.92 | 016 | 10651 | 274.09 | 45.68 | 19.63 |
| C2 | 477 | 332.06 | 55.35 | 5.04 | C10 | 3249 | 351.19 | 59.53 | 7.79 | C16 | 2601 | 254.78 | 42.46 | 17.29 |
| C2 | 489 | 124.09 | 20.68 | 23.51 | C11 | 2738 | 233.39 | 38.9 | 14.68 | C16 | 2629 | 57.02 | 9.5 | 4.30 |
| C2 | 491 | 59.89 | 9.48 | 2.86 | C11 | 2753 | 107.69 | 17.95 | 13.34 | C17 | 2620 | 123.30 | 20.55 | 4.85 |
| C2 | 493 | 99.94 | 16.84 | 11.37 | C11 | 2748 | 101.93 | 31.15 | 14.09 | C17 | 2622 | 130.58 | 21.76 | 20.42 |
| C2 | 499 | 9.35 | 1.56 | 15.20 | C11 | 2719 | 11229 | 18.72 | 5.50 | C17 | 2026 | 124.48 | 20.75 | 10.18 |
| C2 | 500 | 10320 | 17.2 | 6.51 | D11 | 5845 | 4973.19 | 82&87 | 117.18 | C17 | 2637 | 171.60 | 28.6 | 21.56 |
| C3 | 505 | 9.23 | 1.54 | 11.17 | C11 | 2731 | 343.88 | 57.31 | 54.80 | C17 | 2611 | 619.40 | 103.23 | 95.49 |
| C3 | 68 | 185.13 | 30.86 | 251 | C11 | 2741 | 153.01 | 25.5 | 10.65 | C17 | 2640 | 6922 | 14.87 | 3.53 |
| C3 | 43 | 22.82 | 3.8 | 3.02 | C11 | 2725 | 105.9 | 1.61 | 4.59 | C17 | 2655 | 78.92 | 1282 | 5.49 |
| C3 | 1093 | 239.79 | 39.97 | 723 | C11 | 2747 | 222.94 | 37.16 | 6.70 | C17 | 2610 | 11723 | 19.54 | 5.55 |
| C3 | 197 | 25.64 | 4.27 | 2.32 | C11 | 2754 | 72.01 | 12 | 2.74 | C17 | 2658 | 109.19 | 28.2 | 5.60 |
| C3 | 689 | 91.65 | 15.27 | 4.12 PI 4 | C11 | 2743 | 1.6 | 28.14 | 6.16 | D17 | 10687 | 296.18 | 49.7 | 24.54 |
| C3 | 765 | 195.15 | 32.69 | 11.40 | C11 | 2772 | 195.72 | 32.62 | 4.40 | 018 | 11261 | 406.53 | 88.09 | 12.08 |
| C3 | 862 | 225.04 | 37.51 | 17.69 | C12 | 2758 | 24928 | 41.55 | 21.37 | C18 | 2714 | 174.01 | 29 | 6.48 |
| C3 | 943 | 323.18 | 53.86 | 9.61 | C12 | 2759 | 123.94 | 20.66 | 19.69 | C18 | 2718 | 147.48 | 24.58 | 12.37 |
| C3 | 964 | 114.03 | 19.01 | 5.18 | C12 | 2763 | 94.37 | 15.73 | 7.87 | C18 | 2717 | 229.42 | 3824 | 13.88 |
| C4 | 195 | 107.97 | 17.99 | 3.13 | C12 | 2762 | 163.63 | 27.27 | 20.57 | C18 | 2686 | 155.92 | 25.99 | 8.91 |
| C4 | 181 | 63.41 | 13.9 | 1.85 | C12 | 7615 | 271.62 | 45.3 | 17.31 | C18 | 2572 | 86.56 | 16.09 | 4.51 |
| C4 | 183 | 21.42 | 3.57 | 6.40 | C12 | 2769 | 120.17 | 20.03 | 7.86 | C18 | 2716 | 62.03 | 10.34 | 2.69 |
| D4 | 1089 | 157.61 | 26.3 | 13.45 | C12 | 2763 | 187.01 | 3127 | 6.32 | C18 | 2591 | 119.67 | 19.94 | 19.48 |
| C4 | 322 | 109.97 | 18.33 | 3.11 | C12 | 2773 | 139.37 | 2323 | 1322 | C18 | 2715 | 383.68 | 58.98 | 10.63 |
| C4 | 528 | 97.11 | 16.19 | 3.30 | C12 | 2770 | 119.49 | 19.92 | 1.65 | C18 | 2578 | 293.69 | 47.28 | 9.92 |
| C4 | 548 | 3.26 | 0.55 | 3.98 | C12 | 2771 | 221.10 | 36.85 | 13.85 | C18 | 2712 | 380.87 | 63.45 | 12.11 |
| C5 | 369 | 166.90 | 28.15 | 299 | C12 | 2774 | 19621 | 3272 | 15.40 PI 6 | C19 | 2684 | 26824 | 26.38 | 12.33 |
| C5 | 14 | 36.30 | 6.05 | 7.23 | C13 | 2790 | 228.57 | 38.1 | 3.66 | C19 | 11464 | 207.52 | 47.71 | 32.32 |
| C5 | 56 | 148.61 | 24.77 | 3.77 | C13 | 2784 | 96.19 | 16.03 | 11.41 | C19 | 2681 | 226.12 | 34.59 | 17.11 |
| C5 | 305 | 169.0 | 31.6 | 15.91 | C13 | 2788 | 12315 | 20.54 | 17.01 | C19 | 2683 | 168.12 | 37.69 | 12.51 |
| C5 | 1090 | 39262 | 65.44 | 19.55 | C13 | 2783 | 8.43 | 11.07 | 5.43 | C19 | 2667 | 199.65 | 28.02 | 3.65 |
| C5 | 810 | 34926 | 58.21 | 6.61 | C13 | 2775 | 152.61 | 25.43 | 6.82 | C19 | 2663 | 265.47 | 33.31 | 59.81 |
| PI 2 | 343 | 361.84 | 60.31 | 6.57 | D13 | 8094 | 323.63 | 53.94 | 48.56 | C19 | 2660 | 21299 | 44.25 | 10.46 |
| C6 | 111 | 222.05 | 37.01 | 8.78 | C13 | 2785 | 9.13 | 14.86 | 9.31 | C19 | 2676 | 155.91 | 35.5 | 3.79 |
| C6 | 322 | 259.53 | 43.26 | 4.63 | C13 | 2786 | 142.54 | 23.76 | 11.99 | C19 | 2665 | 261.10 | 27.65 | 11.00 |
| C6 | 326 | 4928.73 | 821.12 | 26.35 | C13 | 2781 | 86.10 | 14.35 | 9.43 | C19 | 2674 | 87.94 | 43.52 | 20.22 |
| C6 | 328 | 416.89 | 69.45 | 233 | C13 | | 215.39 | 35.9 | 13.76 | C20 | 2661 | 199.87 | 14.66 | 14.13 |
| C6 | 1096 | 163.02 | 271.67 | 9.20 | C14 | 2570 | 21.36 | 35.23 | 8.01 | C20 | 2641 | 253.45 | 33.31 | 12.76 |
| C6 | 1711 | 244.40 | 40.73 | 13.65 | C14 | 2564 | 157.19 | 26.2 | 23.84 | C20 | 2614 | 2.82 | 42.24 | 4.96 |
| C7 | 2565 | 259.53 | 43.25 | 17.44 | C14 | 2553 | 174.81 | 29.13 | 8.50 | D20 | 11491 | 483.51 | 80.58 | 40.89 |

TABLE 1-continued

| | SAMPLE ID | Dimeric INHIBIN pg/6 ul | Dimeric inhibin ng/ml | Beta-hCG mIU/ml | | SAMPLE ID | Dimeric INHIBIN pg/6 ul | Dimeric inhibin ng/ml | Beta-hCG mIU/ml | | SAMPLE ID | Dimeric INHIBIN pg/6 ul | Dimeric inhibin ng/ml | Beta-hCG mIU/ml |
|---|---|---|---|---|---|---|---|---|---|---|---|---|---|---|
| C7 | 2550 | 141.39 | 23.56 | 4.83 | C14 | 2563 | 16129 | 26.88 | 14.09 | C20 | 2645 | 104.49 | 17.41 | 3.77 |
| C7 | 2548 | 200.40 | 33.4 | 9.11 | C14 | 2554 | 113.72 | 18.95 | 6.63 | C20 | 2644 | 170.29 | 28.38 | 5.84 |
| C7 | 2544 | 69.91 | 14.99 | 8.38 | C14 | 2569 | 174.81 | 29.13 | 9.39 | C20 | 2667 | 200.96 | 33.49 | 3.38 |
| C7 | 2534 | 281.32 | 46.89 | 10.60 | C14 | 2562 | 82.37 | 13.73 | 6.17 | C20 | 2665 | 153.87 | 25.65 | 23.12 |
| C7 | 2568 | 313.10 | 52.18 | 7.16 | D14 | 10348 | 177.73 | 29.62 | 14.38 | C20 | 2639 | 130.63 | 21.81 | 5.55 |
| C7 | 2573 | 176.15 | 29.36 | 8.80 | C14 | 2566 | 5720 | 9.53 | 7.55 | C20 | 2618 | 50.48 | 8.41 | 14.19 |
| C7 | 2583 | 188.60 | 31.43 | 10.38 | C14 | 2560 | 152.96 | 25.5 | 10.06 | C20 | 2628 | 174.89 | 29.11 | 4.27 |
| C7 | 2547 | 229.00 | 37.67 | 11.25 | C14 | 2552 | 237.37 | 39.56 | 8.06 | C20 | 2628 | 109.95 | 18.33 | 2.78 |
| C7 | 2536 | 140.05 | 23.34 | 11.81 | C15 | 2606 | 155.48 | 25.91 | 25.13 | C21 | 3206 | 301.55 | 50.26 | 12.26 |
| C8 | 2650 | 185.95 | 27.61 | 7.73 | C15 | 2546 | 183.69 | 27.28 | 10.24 | C21 | 3223 | 113.25 | 18.87 | 43.30 |
| C8 | 2278 | 428.97 | 71.5 | 21.02 | C15 | 2528 | 212.50 | 35.42 | 75.30 | C21 | 3232 | 141.81 | 23.63 | 4.49 |
| C8 | 2647 | 495.26 | 82.54 | 51.35 | C15 | 2545 | 102.38 | 17.06 | 9.85 | C21 | 4096 | 294.99 | 49.17 | 14.58 |
| C8 | 2649 | 122.28 | 20.38 | 18.16 | C15 | 2521 | 118.58 | 19.43 | 12.52 | C21 | 3221 | 129.72 | 21.62 | 12.06 |
| C8 | 2682 | 391.51 | 65.25 | 10.96 | C15 | 2505 | 189.96 | 27.66 | 15.00 | C21 | 3230 | 97.64 | 16.31 | 25.02 |
| C8 | 2691 | 278.00 | 46.33 | 22.86 | C15 | 2539 | 31.99 | 5.33 | 5.35 | C21 | 3229 | 181.28 | 30.21 | 22.86 |
| C8 | 2651 | 519.81 | 86.6 | 4.76 | C15 | 2523 | 196.86 | 32.81 | 11.01 | C21 | 3228 | 298.37 | 49.73 | 9.93 |
| C8 | 2678 | 297.24 | 49.54 | 7.71 | D15 | 10488 | 190.51 | 31.75 | 17.41 | C21 | 3222 | 451.57 | 75.26 | 28.19 |
| C8 | 2690 | 181.06 | 26.84 | 22.29 | C15 | 2504 | 422.16 | 70.36 | 23.08 | C21 | 3204 | 221.53 | 36.92 | 9.44 |
| C8 | 2659 | 97.20 | 16.2 | 9.72 | C15 | 2516 | 137.18 | 22.86 | 13.35 | C21 | 3213 | 566.40 | 94.4 | 6.51 |
| C8 | 2653 | 193.85 | 32.31 | 12.07 | | | | | | | | | | |
| C9 | 3262 | 229.27 | 38.21 | 17.72 | | | | | | | | | | |
| C9 | 3233 | 113.04 | 18.84 | 6.19 | | | | | | | | | | |
| D9 | 3950 | 457.69 | 76.28 | 137.51 | | | | | | | | | | |
| C9 | 3215 | 145.30 | 24.22 | 13.71 | | | | | | | | | | |
| C9 | 3217 | 357.83 | 59.64 | 4.73 | | | | | | | | | | |
| C9 | 3261 | 162.37 | 27.06 | 6.49 | | | | | | | | | | |
| C9 | 3214 | 962.44 | 143.74 | 27.65 | | | | | | | | | | |
| C9 | 2793 | 122.27 | 20.38 | 9.25 | | | | | | | | | | |
| C9 | 3224 | 94.55 | 15.76 | 4.00 | | | | | | | | | | |
| C9 | 3271 | 111.73 | 18.62 | 5.18 | | | | | | | | | | |
| C9 | 2800 | 240.44 | 40.07 | 29.14 | | | | | | | | | | |

Median regression equations were derived from the concentrations of dimeric inhibin and free-beta hCG by linear regression of the natural log of the median concentration found at each week of gestation against the gestational age in days, weighted by the number of contributory samples at each week of gestation. The regression equations used are shown in Table 2.

TABLE 2

Median regressions

| n | median gestation in weeks | dimeric inhibin ng/ml | free-beta hCG mIU/ml |
|---|---|---|---|
| 5 | 13 | 27.82 | 12.73 |
| 120 | 16 | 26.08 | 10.35 |
| 40 | 17 | 29.23 | 9.18 |
| 14 | 19 | 17.09 | 3.64 |
| 5 | 20 | 28.15 | 6.61 |
| 3 | 21 | 43.25 | 6.57 |
| 1 | 22 | 69.45 | 2.33 |
| 1 | 24 | 821.12 | 26.35 |

Weighted median regressions equations

| | dimeric inhibin | free-beta hCG |
|---|---|---|
| n | 189 | 189 |
| correlation coefficient | 0.1600 | 0.8115 |
| a | −0.00254 | −0.02558 |
| SE of a | 0.00115 | 0.00135 |
| b | 3.56771 | 5.25899 |
| SE of b | 0.14211 | 0.16705 | model: ln (median) - a * GA (in days) + b

Figure 2:
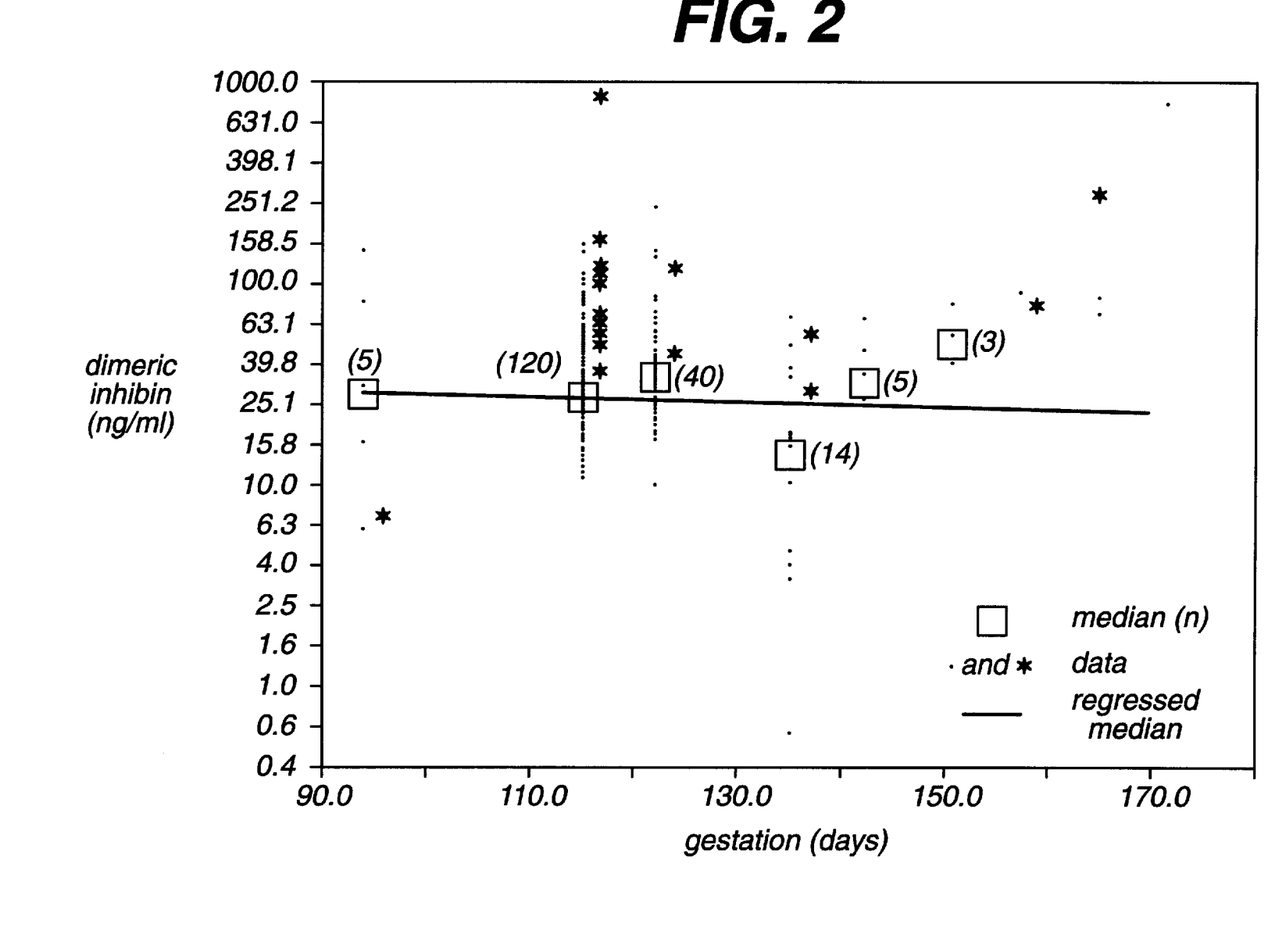
FIG. 2 is a graph of median dimeric inhibin concentration against gestational age.
Figure 3:
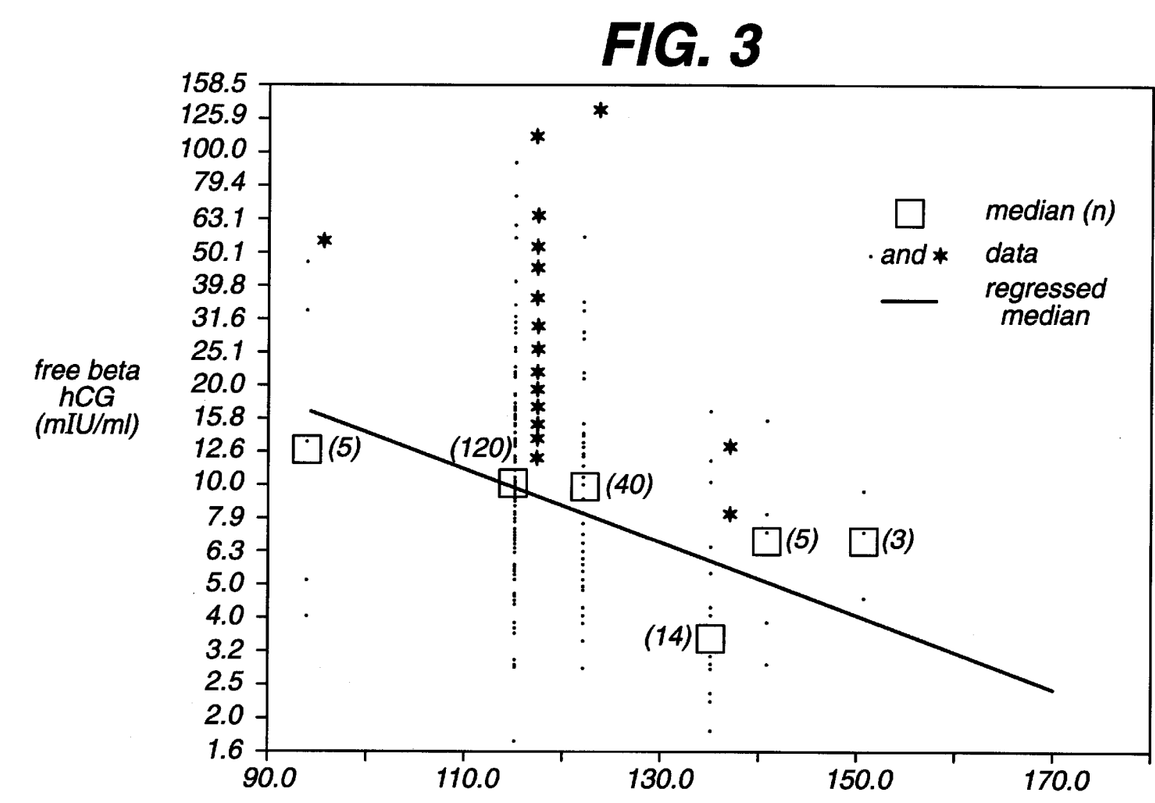
FIG. 3 is a graph of free-beta hCG concentration against gestational age.

The median dimeric inhibin concentration showed little variation with gestational age as shown in FIG. 2. In contrast free-beta hCG concentrations showed a marked decline in concentration over the days of gestation studied as shown in FIG. 3.

MoM values were calculated by dividing each concentration by the expected normal median concentration at that gestational age, the latter being derived from the regression equations shown in Table 2. The median MoM for dimeric inhibin in Downs Syndrome cases was significantly elevated at 1.878 MoM (95% Cl 1.539–2.751) compared to unaffected controls (median MoM 1.30305, 95% Cl 0.9320–1.0960). Similarly free-beta hCG MoM in cases was also significantly elevated at 2.2687 MoM (95% Cl 1.5870–3.2470) compared to controls (median MoM 1.0310, 95% Cl 0.9090–1.1210).

Figure 4:
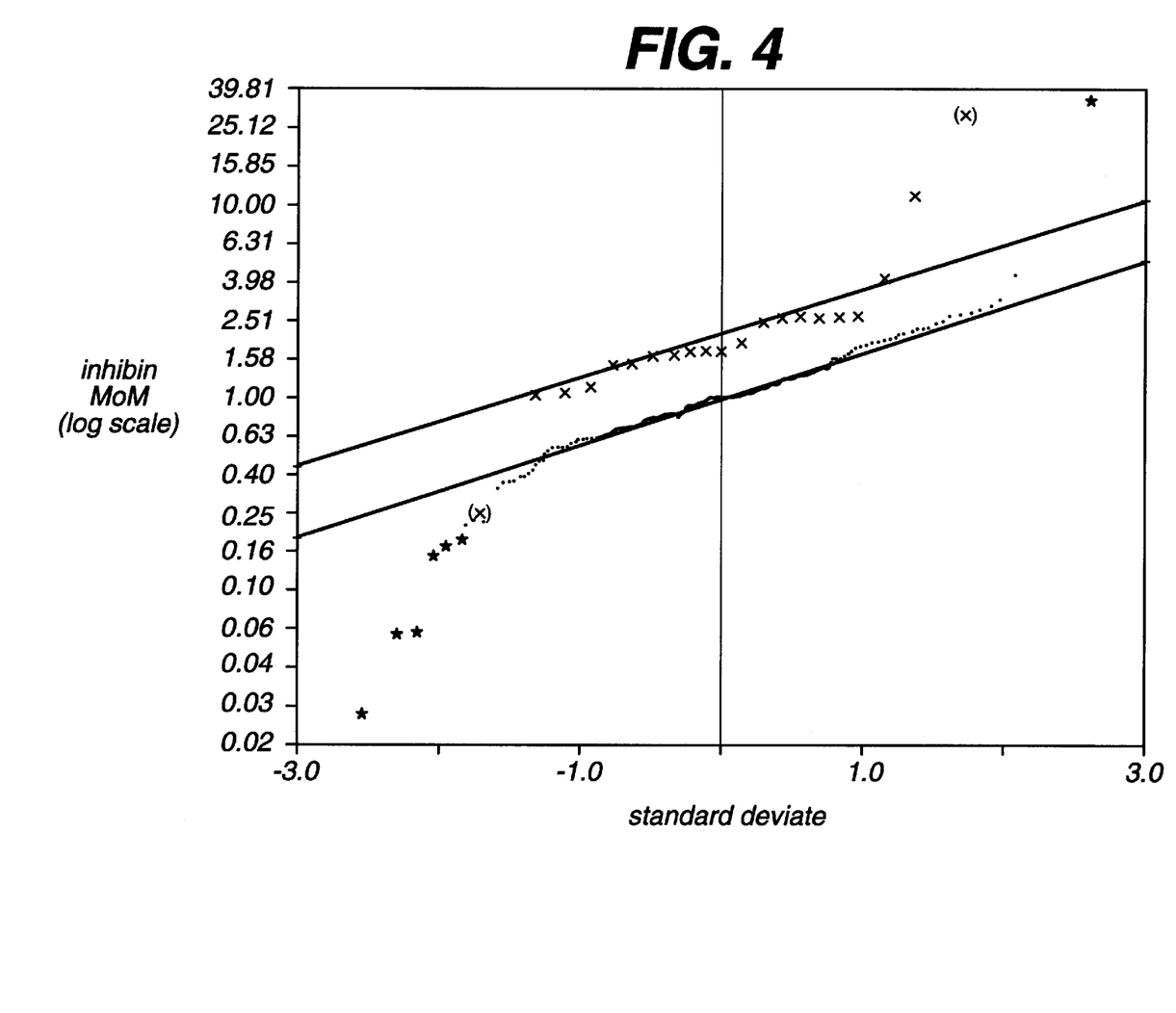
FIG. 4 is a graph of normal probability distribution of dimeric inhibin MoM.
Figure 5:
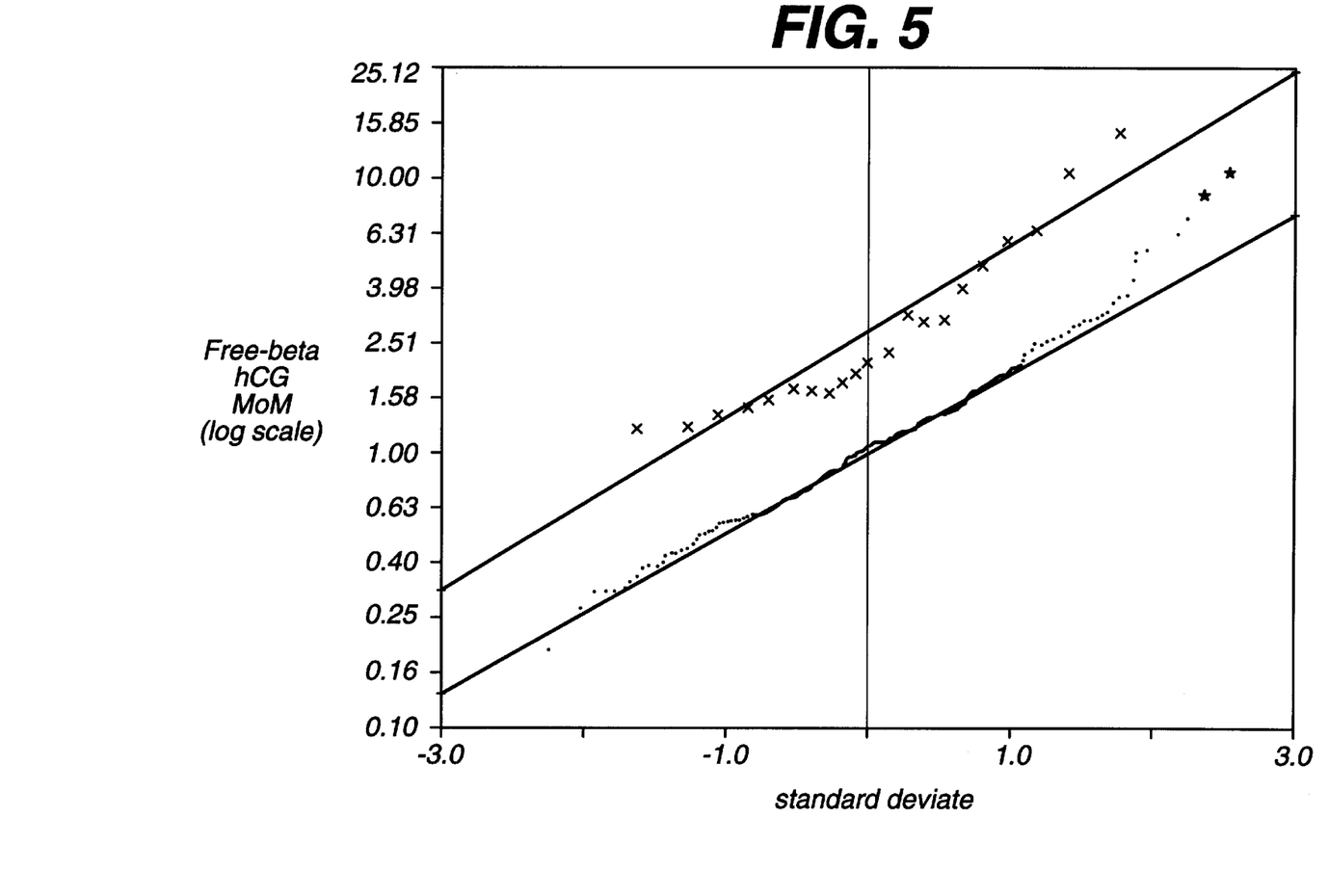
FIG. 5 is a graph of normal probability distribution of free-beta hCG MoM.

Normal probability plots of both dimeric inhibin and free-beta hCG MoM showed log Gaussian distributions for both cases and controls (FIGS. 4 and 5 respectively). The mean and standard deviations of the natural log of the MoM for both dimeric inhibin and free-beta hCG were calculated after exclusion of outliers greater than 3 standard deviations from the mean (Healy, Clinical Chem., 25, 675–7), 1979). The correlation between the natural log of dimeric inhibin and free-beta MoM was 0.2547 for the unaffected controls and 0.0365 for the Downs Syndrome cases.

A statistical summary of the data is shown in Table 3.

TABLE 3

Statistics

| | dimeric inhibin | | free-beta hCG | |
|---|---|---|---|---|
| | unaffected controls | Downs syndrome | unaffected controls | Downs syndrome |
| number | 189 | 21 | 189 | 21 |
| median | 1.0305 | 1.8784 | 1.0310 | 2.2687 |
| 95% Cl median | 0.9320 | 1.5390 | 0.9090 | 1.5870 |
| | 1.0960 | 2.7510 | 1.1210 | 3.2470 |
| 10th centile | 0.4686 | 1.0939 | 0.4445 | 1.2825 |
| 90th centile | 3.3732 | 7.9258 | 2.4410 | 8.8951 |
| intercentile ln (sd) | 0.6160 | 0.7727 | 0.6645 | 0.7556 |
| raw ln (mean) | −0.0233 | 0.8077 | 0.0287 | 1.0206 |
| raw ln (sd) | 0.7775 | 0.9337 | 0.7054 | 0.7230 |
| low outliers | 6 | 1 | 0 | 0 |
| high outliers | 1 | 1 | 2 | 0 |
| trimmed ln (mean) | 0.0392 | 0.7878 | 0.0042 | 1.0206 |
| 95% Cl ln (mean) | −0.0440 | 0.5422 | −0.0915 | 0.7114 |
| | 0.1225 | 1.0334 | 0.0999 | 1.3299 |
| trimmed ln (sd) | 0.5729 | 0.5461 | 0.6679 | 0.7230 |
| trimmed sample | 180 | 19 | | |
| correlation | 0.2547 | 0.0365 | | | trimmed at 10%; outliers ± 3.0 sds

Monte Carlo simulation techniques were employed to estimate the detection rates for Downs Syndrome that would be seen if the combination of free-beta hCG and dimeric inhibin were applied to the general population of pregnant women. Briefly, using the observed bivariate statistical distributions as a seed, random samples were drawn from these distributions corresponding in size to the original data set of 189 controls and 21 cases. New statistical distributions were calculated from these simulated data sets. 20,000 sets of cases and controls were then drawn from these populations and the likelihood ratios calculated for each sample and multiplied by the a priori age risk for women of different ages to,give a combined age and biochemical marker risk. These were weighted by the numbers of pregnant women of different ages seen in the general population for England and Wales for the period 1986–1988 (Office of Population Census and Surveys (OPCS), 1987–1989) to give distributions of risks within the general population.

Figure 6:
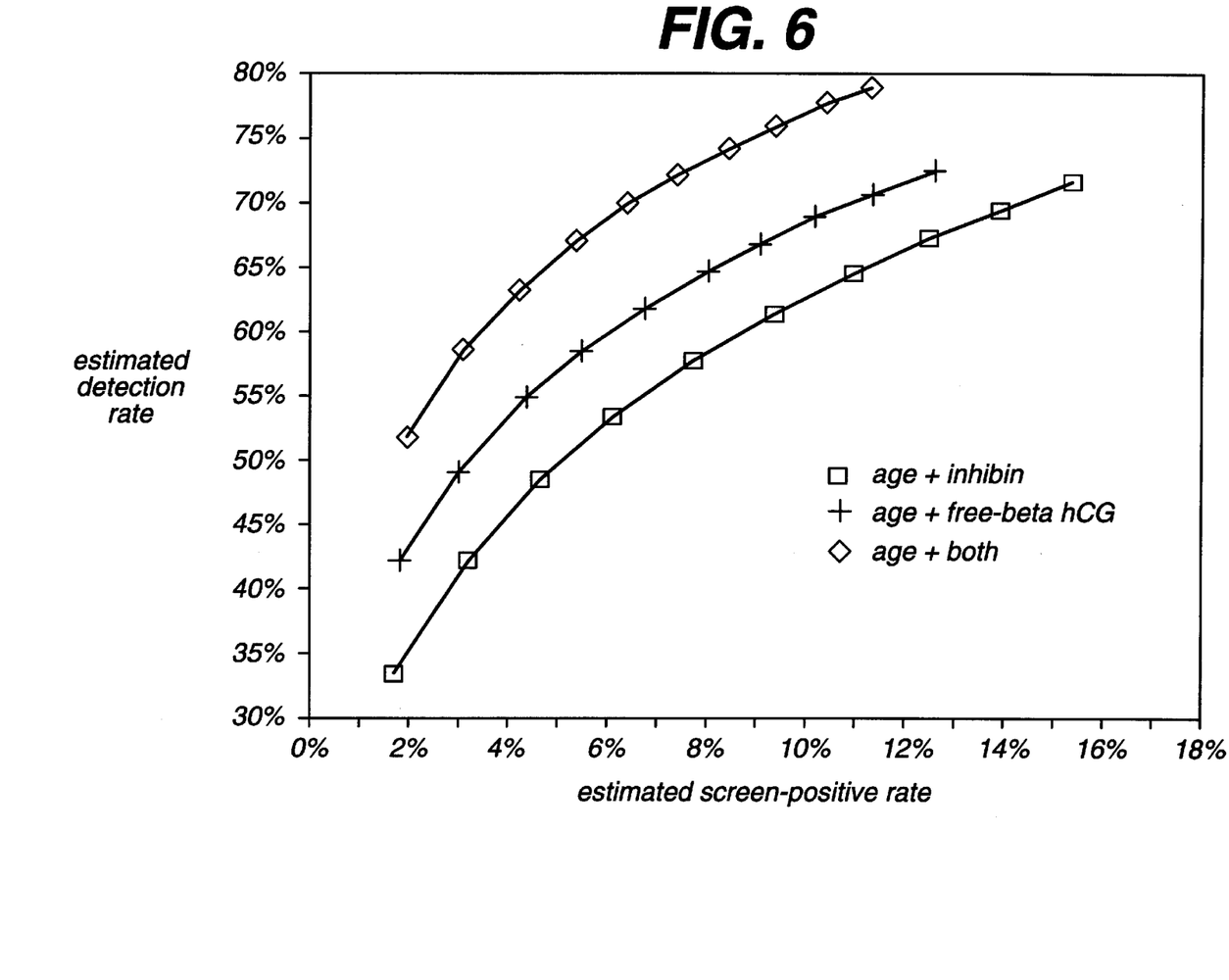
FIG. 6 is a receiver operating characteristic curve (ROC).

100 such simulations allowed for the calculation of the detection rate (sensitivity) of the test in relation to the false-positive rate (1-specificity) for different Downs Syndrome risk cut-off levels, together with the associated 95% CI. These data are shown graphically in the receiver operating characteristic curve (ROC) shown in FIG. 6. A summary of the data is shown in Table 4.

TABLE 4

Detection rates (by Monte-Carlo simulation)

| combination maternal age and . . . | detection rate | standard error | 95% Cl |
|---|---|---|---|
| dimeric inhibin | 50.9% | 6.2% | 38.41%–63.29% |
| free-beta hCG | 57.6% | 7.7% | 42.29%–72.90% |
| inhibin and free-beta hCG ± | 66.4% | 8.1% | 50.15%–82.68% |
| inhibin | 8.82% | 3.6% | 1.54%–16.10% | at an overall 5% screen positive rate
based on 100 Monte Carlo simulations of 21 affected and 189 unaffected cases modelled against term risks for the population of England and Wales for the period 1986–1988

At a 5% screen-positive rate maternal age and dimeric inhibin would be expected to detect 50.9% (95% CI 38.4% −63.3%) o f Downs Syndrome affected pregnancies. Using maternal age and free-beta hCG the detection rate would be 57.6% (95% CI 42.3% to 72.9%) for the same 5% screen-positive rate. The highest detection rate would be achieved using both markers in combination with maternal age. At the same 5% screen-positive rate the detection rate would be 66.4% (95% CI 50.2% –82.7%). The increase seen by adding dimeric inhibin to a combination of maternal age and free-beta hCG is statistically significant (mean increase 8.8%, 95% CI 1.5% –16.1%).

The data presented in this study demonstrate that circulating dimeric inhibin levels in maternal serum of a woman carrying a child is an index of the risk of the child being affected by Downs's Syndrome. Furthermore, the dimeric inhibin result s may also be combined[]with other pregnancy specific analytes such as free beta-hCG to improve the detection rate of Downs affected pregnancies.

The stability of the regressed median of the dimeric inhibin concentrations (within the window of days of gestation examined) translates into a lower dependence upon actual age of gestation compared with other analytes such as free-beta hCG (in this study).

The use of a dimeric inhibin measurement in maternal serum combined with maternal age (in the present study) results in 10% more Downs affected pregnancies being detected at the 5% false positive level than was previously reported (van Lith, Pratt, Beekhuis and Mantingh, Prenatal Diagnosis, 12, 801–6, 1992) who utilized the alpha-specific two-site inhibin assay. The accuracy of detection rate can be improved by inclusion of other analyte results such as free beta-hCG. This improvement is enhanced by a low correlation between the free-beta hCG and dimeric inhibin values in contrast to the data reported in previous studies (Spencer, Wood and Anthony, Anal. clin. Biochem., 30, 219–20, 1993).

In conclusion, the data presented in this study have demonstrated that maternal immunoreactive dimeric inhibin concentration is indeed a useful index of the risk of a woman carrying an unborn child affected by Downs Syndrome. Further improvements in the detection rate of the Downs affected pregnancies can be made by combining the dimeric inhibin data with that of another analyte (free beta-hCG in the above example). Dimeric inhibin determinations will therefore be useful as an additional biochemical marker in Downs Syndrome screening programmes.

We claim:

1. A method for antenatal risk assessment for chromosomal abnormality in a fetus, comprising:
   A) calculating a pregnant patient's prior risk of carrying a fetus having said chromosomal abnormality,
   B) measuring said pregnant patient's blood for a concentration of dimeric inhibin,
   C) calculating a normalized value of said concentration by dividing said concentration by a median value found in a population of women with unaffected pregnancies and same gestational age as said pregnant patient,
   D) calculating a first probability that the corrected normalized value is part of a Gaussian distribution of values found in unaffected pregnancies,
   E) calculating a second probability that the corrected normalized value is a part of a Gaussian distribution of values found in pregnancies with said chromosomal abnormality,
   F) calculating a likelihood ratio, said likelihood ratio being said first probability divided by said second probability, and
   G) modifying the prior risk by the likelihood ratio.

2. The method according to claim 1 wherein step (B) further comprises measuring said patient's blood for a concentration of a marker selected from the group consisting of intact hCG, alphafetoprotein, and unconjugated estriol.

3. The method according claim 1 wherein the chromosomal abnormality is selected from the group consisting of: Down Syndrome, Trisomy 18, Trisomy 13, and Turner Syndrome.

4. The method according to claim 2 wherein the chromosomal abnormality is selected from the group consisting of Down Syndrome, Trisomy 18, Trisomy 13, and Turner Syndrome.

5. An apparatus comprising: a means for obtaining measurements of a pregnant patient's blood concentration of dimeric inhibin and a computer programmed to carry out a method for antenatal risk assessment for chromosomal abnormality in a fetus, said method comprising the following steps:
   A) calculating a pregnant patient's prior risk of carrying a fetus having said chromosomal abnormality,
   B) receiving a measurement of said pregnant patient's blood for a concentration of dimeric inhibin,
   C) calculating a normalized value of said concentration by dividing said concentration by a median value found in a population of women with unaffected pregnancies and same gestational age as said pregnant patient,
   D) calculating a first probability that the corrected normalized value is part of a Gaussian distribution of values found in unaffected pregnancies,
   E) calculating a second probability that the corrected normalized value is a part of a Gaussian distribution of values found in pregnancies with said chromosomal abnormality,
   F) calculating a likelihood ratio, said likelihood ratio being said first probability divided by said second probability, and
   G) modifying the prior risk by the likelihood ratio.

* * * * *

UNITED STATES PATENT AND TRADEMARK OFFICE
CERTIFICATE OF CORRECTION

PATENT NO : 6,022,695
DATED : February 8, 2000
INVENTOR(S): Beard, et al.

It is certified that error appears in the above-identified patent and that said Letters Patent is hereby corrected as shown below: On the title page: Item [54] and Col. 1, line 3,

TITLE "ANTENATAL RISK ASSESSMENT SCREENING FOR PREGNANCY ABNORMALITIES"

SHOULD BE CORRECTED TO PRENATAL RISK ASSESSMENT FOR FETAL ABNORMALITIES

USING DIMERIC INHIBIN DATA

Signed and Sealed this

Ninth Day of January, 2001

Attest:

Q. TODD DICKINSON

Attesting Officer

Commissioner of Patents and Trademarks